United States Patent

Rovnyak

[11] 4,178,379
[45] Dec. 11, 1979

[54] SUBSTITUTED PYRANO[4,3-c]PYRAZOLES, COMPOSITIONS CONTAINING SAME, AND METHOD OF USE

[75] Inventor: George C. Rovnyak, Hopewell, N.J.

[73] Assignee: E. R. Squibb & Sons, Inc., Princeton, N.J.

[21] Appl. No.: 913,268

[22] Filed: Jun. 7, 1978

[51] Int. Cl.$^2$ .................. C07D 491/04; C07D 495/04
[52] U.S. Cl. ............................... 424/273 P; 542/449; 542/450; 548/370
[58] Field of Search ................ 260/449, 450; 548/370; 424/273 P; 542/449, 450

[56] References Cited

U.S. PATENT DOCUMENTS

| | | | |
|---|---|---|---|
| 3,624,102 | 11/1971 | Brown et al. | 548/370 |
| 3,843,666 | 10/1974 | Coombs et al. | 542/449 X |
| 3,962,222 | 6/1976 | Krapcho et al. | 424/273 P |
| 3,979,381 | 9/1976 | Rovnyak | 542/449 |
| 4,003,890 | 1/1977 | Rovnyak | 542/449 |
| 4,042,373 | 8/1977 | Moje | 548/370 X |

Primary Examiner—Arthur P. Demers

Attorney, Agent, or Firm—Lawrence S. Levinson; Burton Rodney

[57] ABSTRACT

2,4,6,7-Tetrahydropyrano[4,3-c]pyrazoles are provided having the formula

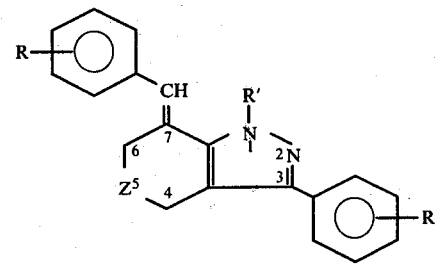

wherein Z is O, S, SO or SO$_2$; R is H, halo, lower alkyl, lower alkoxy, lower alkanoyl, aroyl, cyano or CF$_3$; and R' is H, lower alkyl, aryl-lower alkyl, aryl or halo-lower alkyl. In addition, pharmaceutical compositions containing the above compounds and a method of using same to treat inflammatory conditions in mammalian species is also provided.

14 Claims, No Drawings

SUBSTITUTED PYRANO[4,3-c]PYRAZOLES, COMPOSITIONS CONTAINING SAME, AND METHOD OF USE

FIELD OF THE INVENTION

The present invention relates to substituted pyrano[4,3-c]pyrazoles, and more particularly to 2,4,6,7-tetrahydropyrano[4,3-c]pyrazoles, anti-inflammatory compositions containing same, and to a method for treatment of inflammatory conditions employing the above compounds.

BACKGROUND OF THE INVENTION

U.S. Pat. No. 3,979,381 to Rovnyak discloses hexahydrothiopyrano[4,3-c]pyrazoles of the structure

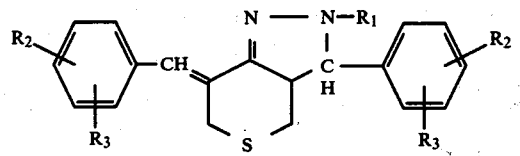

the salts thereof, and the 5-oxide and 5,5-dioxide thereof, wherein $R_1$ is hydrogen, alkyl, aryl, arylalkyl, or acyl; and $R_2$ and $R_3$ are the same or different and are hydrogen, alkyl, hydroxy, alkoxy, alkylthio, alkylsulfinyl, trifluoromethyl, halogen, acyl, cyano, nitro, or dialkylamino.

U.S. Pat. No. 4,003,890 to Rovnyak discloses hexahydropyrano[4,3-c]pyrazoles of the structure

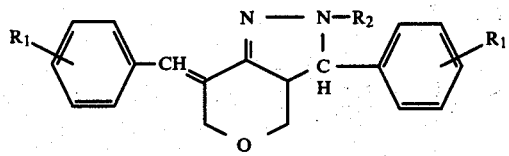

wherein $R_1$ is hydrogen, hydroxy, alkyl, alkoxy, alkylthio, trifluoromethyl, halogen, nitro, cyano, dialkylamino or alkylsulfinyl; and $R_2$ is hydrogen, alkyl, aryl, arylalkyl, acyl or an aminoalkylene.

The above compounds are disclosed to be useful as anti-inflammatory agents.

It has been found that during the preparation of the above Rovnyak compounds as disclosed in the U.S. Pat. Nos. 3,979,381 and 4,003,890, the corresponding tetrahydropyrano- and thiopyrano-pyrazole analogs thereof are also formed. However, the tetrahydro analogs are not isolated from the reaction mixture. In addition, these patents do not disclose a utility for such analogs.

DESCRIPTION OF THE INVENTION

The 2,4,6,7-tetrahydropyrano[4,3-c]pyrazoles of the invention have the following formula

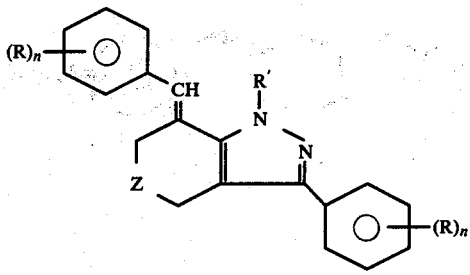

wherein Z is O, S, SO or $SO_2$, R is hydrogen, halogen, lower alkyl, lower alkoxy, lower alkanoyl, aroyl, cyano or trifluoromethyl, and R' is hydrogen, lower alkyl, aryl-lower alkyl, aryl, or halo-lower alkyl, and n is 1 or 2.

Preferred are those compounds wherein Z is S, $SO_2$ or O, R is hydrogen, halogen, trifluoromethyl or lower alkyl and R' is lower alkyl or 2,2,2-trifluoroethyl, and n is 1.

The terms "alkyl" and "alkoxy," as used throughout the specification (by themselves or as part of a larger group) refer to groups having 1 to 8 carbon atoms. Alkyl and alkoxy groups having 1 to 3 carbon atoms are preferred.

The term "aryl," as used throughout the specification (by itself or as part of a larger group) refers to phenyl or phenyl substituted with an alkyl, alkoxy, or halogen group. Phenyl is the preferred aryl group.

The term "halogen," as used throughout the specification, refers to fluorine, chlorine, bromine, and iodine; fluorine and chlorine are preferred.

The term "lower alkanoyl," as used herein, refers to a radical of the structure

wherein $R^2$ is lower alkyl as defined above.

The term "aroyl," as employed herein, refers to a radical of the structure

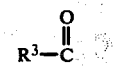

wherein $R^3$ is aryl as defined above.

The compounds of formula I of the invention are formed by reaction of an unsaturated ketone of formula II with a hydrazine of formula III in a molar ratio of from 1:1 to 1:3 preferably in a ratio of from 1:1 to 1:1.5, in a solvent such as methanol, chloroform, 1,2-dichloroethane, carbon disulfide, carbon tetrachloride or tetrahydrofuran. The preferred solvent is tetrahydrofuran, in which the proportion of compound I (relative to compound IA) is greatest. The reaction is performed at reflux temperature for from 1 to 24 hours, preferably for from 1 to 6 hours. The product I and compound IA are separated by fractional crystallization and/or column chromatography and the formula I compound is recovered in crystalline form at least 95% and preferably 99% pure.

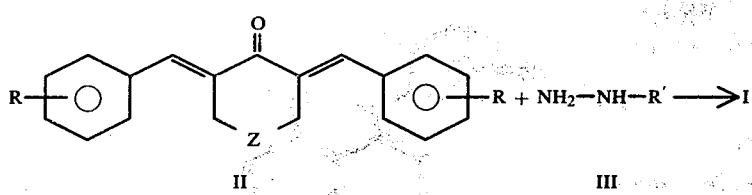

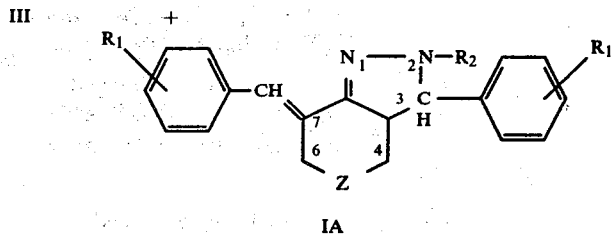

Compounds of formula II are prepared by the method reported in the literature [J.A.C.S. 79, 156 (1957)]. For example, tetrahydro-4H-thiopyran-4-one is reacted with benzaldehyde (optionally substituted) in ethanol and concentrated hydrochloric acid to give compounds of formula II (Z=S). Similarly, compounds of formula II (Z=O, $SO_2$) are formed by substituting the appropriate ketone in place of tetrahydro-4H-thiopyran-4-one. Compounds of formula II (Z=SO) are best prepared by oxidation of compounds of formula II (R=S) with sodium metaperiodate in aqueous methanol. Hydrazines of formula III are made by methods well known in the literature (e.g., see CA, 59:8724f). For example, excess hydrazine is reacted with a compound of formula R'Y, where Y is chlorine or bromine, to give compounds of formula III.

The 5-oxide and 5,5-dioxide derivatives of a thio compound of formula I can, alternatively, be prepared by oxidizing the corresponding thio compound of formula I. Oxidation of a compound of formula I using one equivalent of sodium periodate or hydrogen peroxide yields the corresponding sulfoxide derivative. Oxidation of a thio compound of formula I using potassium permanganate or excess hydrogen peroxide yields the corresponding sulfonyl derivative. Alternatively, the sulfoxide and sulfonyl derivatives can be prepared by treating thio compounds of formula I with m-chloroperbenzoic acid. Treating a thio compound of formula I with an equivalent of m-chloroperbenzoic acid for from 2 to 24 hours at room temperature yields the corresponding sulfoxide derivative. Treating a thio compound of formula I, or a sulfoxide derivative of a compound of formula I, with two equivalents of m-chloroperbenzoic acid for 2 to 24 hours at room temperature (or for a shorter time with slight heating) yields the corresponding sulfonyl derivative.

The compounds of the invention have antiinflammatory activity as measured by the mouse active arthus (MAA) test and are useful an antiinflammatory agents and are effective in the prevention and inhibition of granuloma tissue formation in warm blooded animals, and may be used, for example, in a manner similar to phenylbutazone or indomethacin. They may be used to decrease joint swelling, tenderness, pain and stiffness in mammalian species, such as dogs and monkeys, e.g., in conditions such as rheumatoid arthritis. Compounds of formula I may be compounded for such use according to accepted pharmaceutical practice in oral dosage forms such as tablets, capsules, elixirs or powders or in injectable form for administration of about 100 mg to 2 gm per day, preferably 100 mg to 1 gm per day in two to four divided doses.

The following Examples further illustrate and represent preferred embodiments of the invention. All temperatures are expressed in degrees Centigrade.

EXAMPLE 1

2,4,6,7-Tetrahydro-3-phenyl-7-(phenylmethylene)-1-propylthiopyrano[4,3-c]pyrazole A mixture of tetrahydro-3,5-bis-(phenylmethylene)-4H-thiopyran-4-one (5.84 g, 20 mmole) and n-propyl hydrazine (1.48 g, 20 mmole, CA 59:8724f) in MeOH (100 ml) is heated at reflux temperature for 3 hours. The initial heterogeneous mixture becomes homogeneous after about 0.5 hour. Upon cooling, crystals form and are collected and washed (MeOH) to give 5.0 g, m.p. 106°–118°. Recrystallization from MeOH gives the major product.

The mother liquor is concentrated and upon cooling, 250 mg of the title compound (m.p. 111°–112°) is collected. Two recrystallizations from MeOH yields the title compound as a crystalline material (99% pure), m.p. 115.5°–117.5°.

EXAMPLE 2

3-(4-Chlorophenyl)-7-[(4-chlorophenyl)methylene]-2,4,6,7-tetrahydro-1-propylthiopyrano[4,3-c]pyrazole A. Tetrahydro-3,5-bis-(4-chlorophenylmethylene)-4H-thiopyran-4-one A solution of tetrahydro-4H-thiopyran-4-one (10.0 g, 0.086 mole) and 4-chlorobenzaldehyde (24.0 g, 0.172 mole) in 60 ml ethanol is treated with 6 ml of concentrated HCl and heated at reflux temperature for 2 hours. Upon cooling, 10 g of product is collected. Concentration of the mother liquor and washings to the original volume and adding additional concentrated HCl (4 ml) gives another 12 g of product. The combined crude material, recrystallized from $CHCl_3$/EtOH gives 15 g of product, m.p. 163°–165°.

B. 3-(4-Chlorophenyl)-7-[(4-chlorophenyl)methylene]-2,4,6,7-tetrahydro-1-propylthiopyrano[4,3-c]-pyrazole A mixture of tetrahydro-3,5-bis-(4-chlorophenylmethylene)-4H-thiopyran-4-one (6 g, 16.6 mmole) and N-propylhydrazine (1.3 g, 16.6 mmole) in dichloroethane (100 ml) is heated at reflux temperature for 2.5 hours and cooled to room temperature overnight. The reaction mixture is washed with dilute HCl and water, then dried over $CaCl_2$. After the solvent is removed in vacuo, the residue (yellow solid) is chromatographed on a dry-packed Al₂O₃ column (neutral, activity I). The fractions eluted with 0–5% EtOAc/hexane give the major product. Further elution of the column with EtOAc, then with CHCl₃, and after crystallization from acetone acetonitrile, gives 0.6 g (9%) of the title compound in crystalline form (99% pure) m.p. 192°–194.5°.

EXAMPLE 3

3-(3,4-Dichlorophenyl)-7-[(3,4-dichlorophenyl)methylene]-2,4,6,7-tetrahydro-1-propylthiopyrano[4,3-c]pyrazole A. Tetrahydro-3,5-bis-(3,4-dichlorophenylmethylene)-4H-thiopyran-4-one The procedure as described for tetrahydro-3,5-bis-(4-chlorophenylmethylene)-4H-thiopyran-4-one (see Example 2A above) is used except that 3,4-dichlorobenzaldehyde is employed in place of 4-chlorobenzaldehyde to give a 68% yield of product, m.p. 151°–152.5°.

B. 3-(3,4-Dichlorophenyl)-7-[(3,4-dichlorophenyl)methylene]-2,4,6,7-tetrahydro-1-propylthiopyrano[4,3-c]pyrazole A suspension of tetrahydro-3,5-bis-(3,4-dichlorophenylmethylene)-4H-thiopyran-4-one (6.5 g, 15 mmole) and n-propylhydrazine (1.1 g, 15 mmole) in methanol/chloroform (1:1, 250 ml) is heated at reflux temperature overnight. When the reaction mixture is slightly cooled, unreacted starting material precipitates out and is removed (about 2.2 g) by filtration. The filtrate is concentrated in vacuo and dissolved in CHCl₃ and washed with dilute HCl and water. The organic layer is dried (anhydrous MgSO₄) and concentrated in vacuo to give 5 g of a semi-solid material. This is applied to a wet-packed (hexane) Al₂O₃ column (neutral, activity I), and eluted with 0–100% ether/hexane. The major product is obtained eluting with 10–40% ether/hexane. The later fractions, eluted with 50–80% ether/hexane, are combined, concentrated and the residue crystallized from MeOH/CHCl₃ to give 0.4 g of the product in crystalline form (99% pure), m.p. 161°–162.5° C.

EXAMPLE 4

2,4,6,7-Tetrahydro-3-phenyl-7-(phenylmethylene)-2-propylpyrano[4,3-c]pyrazole

A mixture of tetrahydro-3,5-bis-(phenylmethylene)-4H-pyran-4-one (3.6 g, 13 mmole) and propylhydrazine (1.1 g, 14 mmole) in methanol (250 ml) is heated at reflux temperature for 3–4 hours. MeOH is then removed in vacuo. The residue is dissolved in CHCl₃ and washed with dilute HCl and water, then dried (anhydrous MgSO₄) and concentrated in vacuo to give a yellow oil. When this crude oil is triturated with a small amount of acetonitrile the major product of this reaction precipitates out. The filtrate is concentrated and the residue is applied to a dry-packed Al₂O₃ (Activity I, neutral) column. The fractions eluted with ether are combined and recrystallized first from ether/hexane, then from cyclohexane until a constant m.p. (126.5°–128.5° C.) is reached, giving the product in crystalline form (99% pure).

EXAMPLE 5

2,4,6,7-Tetrahydro-3-(4-methoxyphenyl)-7-[(4-methoxyphenyl)-methylene]-1-propylthiopyrano[4,3-c]pyrazole A mixture of tetrahydro-3,5-bis-(4-methoxyphenylmethylene)-4H-thiopyran-4-one (6 g, 17 mmole) and propylhydrazine (1.4 g, 19 mmole) in methanol (250 ml) is heated at reflux temperature for 4.5 hours. After the reaction mixture is left at room temperature overnight, yellow solids precipitate out and are collectd by filtration. The crude product is applied to a Al₂O₃ column (Activity I, neutral). The major product is eluted with 10–20% ethyl acetate/acetic acid. Continued elution with 10–60% CHCl₃/hexane yields the title compound. Recrystallization from acetone/hexane gives 0.65 g of final product in crystalline form (99% pure), m.p. 131.5°–133.5°.

EXAMPLE 6

2,4,6,7-Tetrahydro-3-(4-methylphenyl)-7-[(4-methylphenyl)-methylene]-1-propylthiopyrano[4,3-c]pyrazole A mixture of tetrahydro-3,5-bis-(4-methylphenylmethylene)-4H-thiopyran-4-one (6.7 g, 20 mmole) and n-propylhydrazine (1.6 g, 22 mmole) in methanol (250 ml) is heated at reflux temperature for 5 hours, then cooled overnight. The pale yellow precipitate is collected by filtration. The filtrate is concentrated to about 50 ml and additional precipitate is again collected by filtration and combined with the previous batch to give 5.5 g of a crude product mixture.

This is chromatographed on a dry-packed Al₂O₃ column (280 g of neutral Al₂O₃, Activity I), and eluted with 0–100% ether/hexane. The major product is eluted with 10–20% ether/hexane.

Column elution is continued with 40–60% ether/hexane. The product obtained is recrystallized from ether/hexane to yield 650 mg of the title compound in crystalline form (99% pure). m.p. 140°–143° C.

EXAMPLE 7

2,4,6,7-Tetrahydro-3-(4-methylphenyl)-7-[(4-methylphenyl)-methylene]-1-propylthiopyrano[4,3-c]pyrazole, 5,5-dioxide A mixture of tetrahydro-3,5-bis-(4-methylphenylmethylene)-4H-thiopyran-4-one-1,1-dioxide (5.5 g, 15 mmole) and n-propylhydrazine (1.5 g, 20 mmole) in methanol (250 ml) is heated at reflux temperature for 1.5 hours, then cooled overnight. Recrystallization of the crude product from acetone/hexane gives a mixture of the major product as fine white needles and the title compound as larger yellow prisms. The latter are separated by a rapid wash of the crude mixture with CHCl₃, the larger crystals of the title compound being dissolved much more slowly and being left behind. These crude crystals are recrystallized from CHCl₃/MeOH to give the title compound (99% pure), m.p. 235°–238°.

EXAMPLE 8

2,4,6,7-Tetrahydro-1-(1-methylethyl-3-[3-(trifluoromethyl)-phenyl]-7-[[3-(trifluoromethyl)phenyl]methylene]thiopyrano-[4,3-c]pyrazole, 5,5-dioxide A. Tetrahydro-3,5-bis-[3-(trifluoromethyl)phenylmethylene]-4H-thiopyran-4-one-1,1-dioxide Tetrahydro-3,5-bis[3-(trifluoromethyl)phenylmethylene]-4H-thiopyran-4-one is prepared as described above for tetrahydro-3,5-bis-(4-chlorophenylmethylene)-4H-thiopyran-4-one, except that 3-(trifluoromethyl)benzaldehyde is employed in place of 4-chlorobenzaldehyde. The product (m.p. 113.5°–116°, 18.0 g, 0.042 mole) in 300 ml of glacial acetic acid is treated with 27 ml of 30% H₂O₂ and heated on a steam bath for 0.5 hour. A small amount of water is added and the solution is cooled in an ice bath. The crystals obtained are recrystallized from CHCl₃/hexane to give 14.5 g (87%) of the title compound, m.p. 154.5°–155.5°.

B. 2,4,6,7-Tetrahydro-1-(1-methylethyl)-3-[3-(trifluoromethyl)phenyl]-7-[[3-(trifluoromethyl)phenyl]-methylene]thiopyrano[4,3-c]-pyrazole, 5,5-dioxide A solution of tetrahydro-3,5-bis-[3-(trifluoromethyl)-phenylmethylene]-4H-thiopyran-4-one-1,1-dioxide (5.1 g, 11 mmole) and isopropylhydrazine (1.0 g, 13 mmole) in 200 ml of methanol is heated at reflux temperature for 3 hours. Water is added (until slightly cloudy) and the solution is allowed to cool to room temperature. There is collected 4 g of crude product mixture. Several crystallizations from ethyl acetate/hexane give the major product.

The mother liquors are concentrated to give a total of ca 2 g of crude minor product. Recrystallization twice from MeOH/H₂O gives 1.2 g (21%) of the title compound (99% pure), m.p. 170°–172°.

EXAMPLE 9

2,4,6,7-Tetrahydro-3-(4-methylphenyl)-7-[(4-methylphenyl)-methylene]-1-(2,2,2-trifluoroethyl)thiopyrano[4,3-c]pyrazole, 5,5-dioxide A stirred suspension of tetrahydro-3,5-bis-(4-methylphenylmethylene)-4H-thiopyran-4-one-1,1-dioxide (7.0 g, 20 mmole) in 150 ml of MeOH is treated with 2,2,2-trifluoroethyl hydrazine (4.1 g, 25 mmole, 70% aqueous solution) in a small volume of MeOH at room temperature. Upon heating at reflux temperature the solution becomes homogeneous, the initially yellow color becoming progressively more pale. After several hours a white solid begins to separate and after 5 hours, the solution is cooled and filtered. The solids, washed with MeOH and hexane and air-dried, give 5.7 g, m.p. 168°–178°. The tlc shows two spots at R_f =0.50 and 0.57 (40% EtOAc/Hexane on silica gel) of about equal intensity (uv visualization). Two recrystallizations from CHCl₃/CCl₄, then from acetone/hexane, give 2.3 g (26%) of the title compound (99% pure) m.p. 190°–192°.

EXAMPLES 10 to 16

Following the procedure of Example 1, but substituting for tetrahydro-3,5-bis-(phenylmethylene)-4H-thiopyran-4-one, the compound shown in Column I of Table I set out below and substituting for n-propyl hydrazine, the compound shown in Column II, the compound of the invention in substantially pure (at least 95% pure) crystalline form is obtained.

TABLE I

| Ex. No. | Column I | | | | Column II | Column III | | | |
|---|---|---|---|---|---|---|---|---|---|
| | n | R(position) | Z | R¹ | NH₂—NH—R¹ R¹ | n | R(position) | Z | R¹ |
| 10. | 1 | CH₃C(=O) | S | H | | as in Column I | | | as in Column II |
| 11. | 1 | C₆H₅C(=O) | SO | C₂H₅ | | | | | |
| 12. | 1 | CN | O | C₆H₅CH₂ | | | | | |
| 13. | 1 | C₂H₅C(=O) | S | C₆H₅ | | | | | |
| 14. | 1 | CN | SO₂ | ClCH₂ | | | | | |
| 15. | 1 | CF₃ | SO | C₆H₅CH₂ | | | | | |
| 16. | 1 | C₂H₅O | O | H | | | | | |

What is claimed is:

1. A compound of the structure

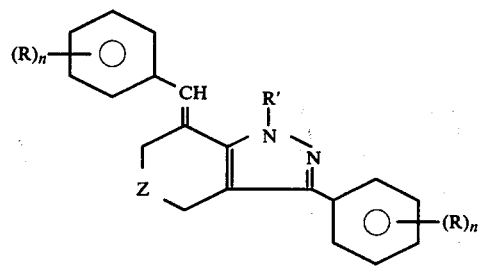

wherein Z is O, S, SO or SO₂, n is 1 or 2, R is hydrogen, halogen, lower alkyl, lower alkoxy, lower alkanoyl, aroyl, cyano or trifluoromethyl, and R' is hydrogen, lower alkyl, aryl-lower alkyl, aryl, or halo-lower alkyl.

2. The compound as defined in claim 1 wherein Z is S, R is in the 3- or 4-position and is halogen or lower alkyl, R' is lower alkyl, and n is 1.

3. The compound as defined in claim 1 in crystalline form at least 95% pure.

4. The compound as defined in claim 3 having the name 2,4,6,7-tetrahydro-3-phenyl-7-(phenylmethylene)-1-propylthiopyrano[4,3-c]pyrazole and a melting point of 115.5°–117.5° C.

5. The compound as defined in claim 3 having the name 3-(4-chlorophenyl)-7-[(4-chlorophenyl)methylene]-2,4,6,7-tetrahydro-1-propylthiopyrano[4,3-c]pyrazole and a melting point of 192-194.5° C.

6. The compound as defined in claim 3 having the name 3-(3,4-dichlorophenyl)-7-[(3,4-dichlorophenyl)methylene]-2,4,6,7-tetrahydro-1-propylthiopyrano[4,3-c]-pyrazole and a melting point of 161°-162.5° C.

7. The compound as defined in claim 3 having the name 2,4,6,7-tetrahydro-3-phenyl-7-(phenylmethylene)-2-propylpyrano[4,3-c]pyrazole and a melting point of 126.5°-128.5° C.

8. The compound as defined in claim 3 having the name 2,4,6,7-tetrahydro-3-(4-methoxyphenyl)-7-[(4-methoxyphenyl)methylene]-1-propylthiopyrano[4,3-c]-pyrazole and a melting point of 131.5°-133.5° C.

9. The compound as defined in claim 3 having the name 2,4,6,7-tetrahydro-3-(4-methylphenyl)-7-[(4-methylphenyl)methylene]-1-propylthiopyrano[4,3-c]-pyrazole and a melting point of 140°-143° C.

10. The compound as defined in claim 3 having the name 2,4,6,7-tetrahydro-3-(4-methylphenyl)-7-[(4-methylphenyl)methylene]-1-propylthiopyrano[4,3-c]-pyrazole, 5,5-dioxide and a melting point of 235°-238° C.

11. The compound as defined in claim 3 having the name 2,4,6,7-tetrahydro-1-(1-methylethyl)-3-[3-(trifluoromethyl)phenyl]-7-[[3-(trifluoromethyl)phenyl]methylene]thipyrano[4,3-c]pyrazole, 5,5-dioxide and a melting point of 170°-172° C.

12. The compound as defined in claim 3 having the name 2,4,6,7-tetrahydro-3-(4-methylphenyl)-7-[(4-methylphenyl)methylene]-1-(2,2,2-trifluoroethyl)-thiopyrano[4,3-c]pyrazole, 5,5-dioxide and a melting point of 190°-192° C.

13. An anti-inflammatory composition comprising a therapeutically effective amount of a compound as defined in claim 1 in a physiologically acceptable carrier therefor.

14. A method for treating an inflammatory condition in a mammalian host, which comprises administering an effective amount of the composition as defined in claim 13.

* * * * *

UNITED STATES PATENT AND TRADEMARK OFFICE
CERTIFICATE OF CORRECTION

PATENT NO. : 4,178,379

DATED : December 11, 1979

INVENTOR(S) : George C. Rovnyak

It is certified that error appears in the above-identified patent and that said Letters Patent are hereby corrected as shown below:

Column 3, line 57, "an" should read --as--.

Column 10, line 7, "thipyrano" should read --thiopyrano--.

Signed and Sealed this

First Day of April 1980

[SEAL]

Attest:

SIDNEY A. DIAMOND

Attesting Officer

Commissioner of Patents and Trademarks